(12) United States Patent
Guo et al.

(10) Patent No.: US 10,178,998 B2
(45) Date of Patent: Jan. 15, 2019

(54) LATERAL GRINDING DRILL WITH CONTINUOUSLY VARIABLE ANGLE AND DRIVING COMPONENT THEREOF

(71) Applicant: Chongqing Xishan Science & Technology Co., Ltd., Chongqing (CN)

(72) Inventors: Yijun Guo, Chongqing (CN); Changfeng Liu, Chongqing (CN); Jinbin Zhang, Chongqing (CN)

(73) Assignee: Chongqing Xishan Science & Technology Co., Ltd. (CN)

( * ) Notice: Subject to any disclaimer, the term of this patent is extended or adjusted under 35 U.S.C. 154(b) by 522 days.

(21) Appl. No.: 14/894,939

(22) PCT Filed: Sep. 26, 2014

(86) PCT No.: PCT/CN2014/087552
§ 371 (c)(1),
(2) Date: Nov. 30, 2015

(87) PCT Pub. No.: WO2015/078229
PCT Pub. Date: Jun. 4, 2015

(65) Prior Publication Data
US 2016/0106442 A1    Apr. 21, 2016

(30) Foreign Application Priority Data

Nov. 29, 2013  (CN) .......................... 2013 1 0632414
Dec. 3, 2013   (CN) .......................... 2013 1 0641876
Jan. 28, 2014  (CN) .......................... 2014 1 0041760

(51) Int. Cl.
*A61B 17/00*    (2006.01)
*A61B 17/16*    (2006.01)
(Continued)

(52) U.S. Cl.
CPC ...... *A61B 17/1631* (2013.01); *A61B 17/1633* (2013.01); *A61B 17/32002* (2013.01);
(Continued)

(58) Field of Classification Search
None
See application file for complete search history.

(56) References Cited

U.S. PATENT DOCUMENTS

| 5,752,973 A | 5/1998 | Kieturakis |
| 8,052,690 B2 | 11/2011 | Berthusen et al. |

(Continued)

FOREIGN PATENT DOCUMENTS

| AU | 2011323989 A1 | 5/2013 |
| CN | 1585623 A | 2/2005 |

(Continued)

OTHER PUBLICATIONS

The Extended European Search Report and Written Opinion for parallel European Patent Application No. 14866116.8, dated Dec. 21, 2016.

(Continued)

*Primary Examiner* — Sameh Boles
(74) *Attorney, Agent, or Firm* — Lerner, David, Littenberg, Krumholz & Mentlik, LLP (57) ABSTRACT

The present invention discloses a lateral grinding drill with continuously variable angle, including a tube body component and a grinding head arranged at the front end of the tube body component, the grinding head being configured to be driven to pitch and rotate on its own axis, the tail end of the grinding head is articulated to the inner tube body along the circumferential direction in a form of transmission, and a flexible transmission part is arranged at least on the front end of the inner tube body, which is configured to be articulated to the tail end of the grinding head and be able to transmit (Continued)

torque. The present invention adopts a direct articulated structure to transmit the transmission between the inner tube body and the grinding head, and can implement pitching motion. A flexible transmission structure is used to compensate the axis deviation caused by the pitching and driving. The transmission structure is simple, and the transmission cycle is short, which facilitates stable control to improve the efficiency of the surgery. In addition, with the structure which can adjust the grinding head in both the pitching and circumferential positions, it achieves the universal direction adjustment of the grinding head, which can have a good adaptability for the surgery position and good accuracy to improve the efficiency in surgery operation, and shorten postoperative recovery time, to alleviate the suffering of the patients while reducing treatment cost.

14 Claims, 2 Drawing Sheets

(51) Int. Cl.
*A61C 3/02* (2006.01)
*A61C 1/18* (2006.01)
*A61B 17/32* (2006.01)
*A61B 17/29* (2006.01)

(52) U.S. Cl.
CPC ............... *A61C 1/188* (2013.01); *A61C 3/02* (2013.01); *A61B 17/1622* (2013.01); *A61B 2017/2927* (2013.01)

(56) References Cited

U.S. PATENT DOCUMENTS

| | | | |
|---|---|---|---|
| 8,221,424 | B2 | 7/2012 | Cha |
| 2003/0097133 | A1 | 5/2003 | Green et al. |
| 2005/0147478 | A1 | 7/2005 | Greenberg |
| 2005/0203527 | A1 | 9/2005 | Carrison et al. |
| 2009/0023988 | A1 | 1/2009 | Korner et al. |
| 2010/0057087 | A1 | 3/2010 | Cha |
| 2011/0152867 | A1* | 6/2011 | Petrzelka ............ A61B 17/1631 606/80 |

FOREIGN PATENT DOCUMENTS

| | | |
|---|---|---|
| CN | 201346224 Y | 11/2009 |
| CN | 201394046 Y | 2/2010 |
| CN | 102210604 A | 10/2011 |
| CN | 102448388 A | 5/2012 |
| CN | 103200885 A | 7/2013 |
| CN | 203388927 U | 1/2014 |
| CN | 103768859 A | 5/2014 |
| EP | 2016913 A1 | 1/2009 |
| EP | 2623049 A1 | 8/2013 |
| EP | 2437627 B1 | 12/2013 |
| JP | H01119241 A | 5/1989 |
| JP | 2005510284 A | 4/2005 |
| WO | 9921686 A1 | 5/1999 |
| WO | 01/060232 A2 | 8/2001 |
| WO | 2005062827 A2 | 7/2005 |
| WO | 2012153319 A1 | 11/2012 |

OTHER PUBLICATIONS

Search Report & First Office Action for Priority Chinese Patent Application No. 201310641876.X, dated Apr. 25, 2016.
Supplementary Search Report & Second Office Action for Priority Chinese Patent Application No. 201310641876.X, dated Jan. 13, 2017.
Third Office Action for Priority Chinese Patent Application No. 201310641876.X, dated May 10, 2017.
Search Report & First Office Action for Priority Chinese Patent Application No. 201410041760.7, dated Jan. 21, 2015.
Office Action for parallel Korean Patent Application No. 10-2015-7034145, dated Oct. 18, 2016.
First Office Action (Notice of Grounds for Rejection) for parallel Japanese Patent Application No. 2016-553696, dated Mar. 7, 2017.
Second Office Action for parallel Japanese Patent Application No. 2016-553696, dated Jun. 20, 2017.
Chinese Office Action for CN Application No. 201310641876.X, dated Nov. 1, 2017.
European Office Action for EP Application No. 17179220.3, dated May 3, 2018.
European Search Report and Written Opinion for EP Application No. 17179219.5, dated Nov. 24, 2017.
European Search Report for EP Application No. 17179220.3, dated Nov. 24, 2017.
Japanese Office Action for JP Application No. 2017110056, dated Dec. 14, 2017.
Japanese Office Action for JP Application No. 2017110065, dated Feb. 20, 2018.
International Search Report for Application No. PCT/CN2014/087552 dated Jan. 4, 2015.

* cited by examiner

LATERAL GRINDING DRILL WITH CONTINUOUSLY VARIABLE ANGLE AND DRIVING COMPONENT THEREOF

CROSS-REFERENCE TO RELATED APPLICATIONS

The present application is a national phase entry under 35 U.S.C. § 371 of International Application No. PCT/CN2014/087552 filed Sep. 26, 2014, which claims priority from Chinese Application Nos. 201310632414.1 filed Nov. 29, 2013; 201310641876.X filed Dec. 3, 2013, and 201410041760.7 filed Jan. 28, 2014, all of which are hereby incorporated herein by reference.

FIELD

The present invention relates to a medical device, and more particularly, to a lateral grinding drill with continuously variable angle used in orthopedics surgery and a driving component.

BACKGROUND

The bone tissue in the body sometimes needs to be grinded in orthopedic surgery. In the prior art, the grinding head is generally driven by a power handle directly to rotate for grinding. Since the grinding head is directly driven by the power handle, and the grinding head is required to extend into the human body, it is difficult to control the grinding head when the grinding head reaches a surgery site that is difficult to observe. Especially when different positions are required to be grinded, the grinding head is hard to be changed to accommodate the positions required to be grinded. Such grinding head is inconvenient to use, causing a low efficiency of the surgery.

In order to solve the above problem, a flexible grinding head appeared. The grinding head can be controlled to perform pitching action in response to changes in positions required to be grinded. The grinding head has a structure with a universal joint for connecting and driving. The structure is complex and its manufacturing process is also complex. With the structure, the radius of the grinding tool is increased, while the above orthopedic surgery generally requires the whole of the grinding tool have a small external diameter, otherwise the grinding tool cannot reach the surgery position, or motion interference can happen during the surgery. Meanwhile, in the structure, a connection structure with a universal joint can be used to implement pitching motion and rotating transmission between the grinding head and the inner tube, but such structure is complex and cannot be controlled stably. In addition, the structure can only implement the pitching action, and cannot implement adaptive operations corresponding to the change of the portion required to be grinded in circumferential direction, so that both the grinding tool and the driving handle should change direction integrally, resulting in inconvenience for use. Further, the driving part for driving the pitching action is relatively primitive, which affects the compactness of the grinding tool.

As a result, there is a requirement to provide a lateral grinding drill with continuously variable angle, which can adjust the position of the grinding head in longitudinal direction and circumferential direction during surgery, have a good adaptability for the surgery position and good accuracy to improve the efficiency in surgery operation, and shorten postoperative recovery time, to alleviate the suffering of the patients while reducing treatment cost. In addition, the whole of the lateral grinding drill with continuously variable angle is detachable, with a simple structure, in which, the transmission chain is short that it is easy for stable control to improve the efficiency of the surgery.

SUMMARY

Based on this, the present invention provide a lateral grinding drill with continuously variable angle, which can adjust the position of the grinding head in longitudinal direction and circumferential direction during surgery, have a good adaptability for the surgery position and good accuracy to improve the efficiency in surgery operation, and shorten postoperative recovery time, to alleviate the suffering of the patients while reducing treatment cost. In addition, the whole of the lateral grinding drill with continuously variable angle is detachable, with a simple structure, in which, the transmission chain is short that it is easy for stable control to improve the efficiency of the surgery.

The lateral grinding drill with continuously variable angle according to the present invention includes a tube body component and a grinding head arranged at the front end of the tube body component, the grinding head being configured to be driven to pitch and rotate on its own axis, wherein the tube body component includes an outer tube body and an inner tube body which is coaxially arranged inside the outer tube body and configured to be rotatablely fit with the outer tube body and the grinding head, the tail end of the grinding head is articulated to the inner tube body to achieve transmission along the circumferential direction, and a flexible transmission part is arranged at least on the front end of the inner tube body, which is configured to be articulated to the tail end of the grinding head and be able to transmit torque.

Further, an articulation groove with an opening end is formed at the tail end of the grinding head, and the front end of the flexible transmission part is provided with a rod-shaped articulation portion which is configured to be rotatablely fit with the flexible transmission part and articulated and fit with the articulation groove.

Further, an articulation groove is formed at the tail end of the grinding head, the front end of the flexible transmission part is provided with a rod-shaped articulation portion which is configured to be rotatablely fit with the flexible transmission part and articulated and fit with the articulation groove, the rod-shaped articulation portion and the flexible transmission part form a T-shaped structure.

Further, the root of the connection between the flexible transmission part and the rod-shaped articulation portion is necking on the T-shaped plane.

Further, the grinding head is provided with a grinding head handle, and the articulation groove is located on the tail end of the grinding head handle; the front end of the outer tube body is articulated with a grinding head mount sheath in a single degree of freedom mode, the grinding head handle is arranged inside the grinding head mount sheath and configure to be rotatablely fit with the grinding head mount sheath in a single degree of freedom mode, and the grinding head has a grinding blade extending out of the grinding head mount sheath; and the flexible transmission part is connected to the front end of the inner tube body, and the rod-shaped articulation portion is integrally formed on the front end of the flexible transmission part.

Further, the outer tube body is configured to be driven to rotate along the circumferential direction, so that the grinding head mount sheath and grinding head are configured to be driven to revolute.

Further, the lateral grinding drill with continuously variable angle further includes a connection handle and a driving component, and the driving component includes a pitching driving component for driving the grinding head mount sheath to pitch and a direction driving component for driving the outer tube body to rotate along the circumferential direction.

The pitching driving component includes a reciprocating middle part and a reciprocating driving part, the front end of the reciprocating middle part is connected to the grinding head mount sheath in a form that the grinding head mount sheath is drivable to pitch, the back end of the reciprocating middle part is drivablely fit with the reciprocating driving part at least in the axial direction, and the reciprocating driving part is fit with the connection handle in a form that the reciprocating driving part is movable relative to the connection handle connection handle.

The direction driving component includes a connection sleeve coaxially fixed to the outer tube body, and a driving sleeve arranged outside the connection sleeve, the driving sleeve is fixed to the connection sleeve in the circumferential direction and is slidable to the connection sleeve in the axial direction, and the driving sleeve is configured to slide along the axial direction to engage with or disengage from the connection handle to achieve limiting or releasing in the circumferential direction.

Further, the driving sleeve is provided with a backward pretightening force which makes the driving sleeve be close to the front end of the connection handle and engage with the connection handle in the circumferential direction; the tail end of the reciprocating middle part is axially fixedly connected with a transition sleeve, a radial driving arm is arranged on the outer circle of the transition sleeve, and the radial driving arm is configured to be rotatablely fit with the reciprocating driving part in a single degree of freedom mode; the reciprocating driving part is a reciprocating driving sleeve with internal threads which match with external threads provided on the connection handle; and a necking portion is arranged on the back end of the driving sleeve, the front end of the reciprocating driving sleeve is arranged outside the outer circle of the necking portion of driving sleeve, and the back end of the reciprocating driving sleeve is arranged outside the connection handle.

The present invention also discloses a lateral grinding drill with continuously variable angle, including a tube body component and a grinding head arranged at the front end of the tube body component, the grinding head being configured to be driven to pitch and rotate on its own axis, the tube body component including an outer tube body and an inner tube body which is coaxially arranged inside the outer tube body and configured to be rotatablely fit with the outer tube body and the grinding head, the front end of the outer tube body being articulated with a grinding head mount sheath in a single degree of freedom mode, the grinding head being provided with a grinding head handle, the grinding head handle is provided with a position-limiting ring which is configured to be rotatablely fit with the grinding head handle in a single degree of freedom mode, and the grinding head handle is arranged inside the grinding head mount sheath through the position-limiting ring in an axial position-limiting form.

Further, the grinding head mount sheath includes an outer sleeve and an inner sleeve arranged inside the outer sleeve, the position-limiting ring is provided with two radially symmetric position-limiting bulges, the outer circle of the grinding head handle is provided with an annular position-limiting groove configured to make the position-limiting ring into place and have extra movement space in radial direction, the inner sleeve is provided with two radially symmetric axial opening grooves, the outer sleeve is provided with a position-limiting through hole radially passing through the outer sleeve, and the outer sleeve is an opening sleeve with an axial opening; and the grinding head handle is arranged inside the inner sleeve, two position-limiting bulges of the position-limiting ring are fit along the axial opening grooves, one of the position-limiting bulges is inserted into the position-limiting through hole, and the other position-limiting bulge abuts on the inner wall of the outer sleeve.

The present invention also discloses a lateral grinding drill with continuously variable angle, including a tube body component and a grinding head arranged at the front end of the tube body component, the grinding head being configured to be driven to pitch and rotate on its own axis, the tube body component including an outer tube body and an inner tube body which is coaxially arranged inside the outer tube body and configured to be rotatablely fit with the outer tube body and the grinding head, the front end of the outer tube body being articulated with a grinding head mount sheath in a single degree of freedom mode, the grinding head being mounted on the grinding head mount sheath and configure to be rotatablely fit with the grinding head mount sheath along the circumferential direction, and the grinding head having a grinding blade extending out of the grinding head mount sheath; and the grinding head mount sheath is provided with a reciprocating middle part configured to drive the grinding head mount sheath to pitch in the rotation direction of the articulation, and the reciprocating middle part at least has movement space in the direction of the pitching motion of the grinding head mount sheath.

Further, the reciprocating middle part is a middle tube body located between the inner tube body and the outer tube body, there is radical movement space between the middle tube body and the inner tube body, and between the middle tube body and the outer tube body, the radical movement space accommodates the radial displacement caused by the middle tube body when the grinding head mount sheath is driven to pitch; and the front end of the middle tube body extends forward to form a pitching articulation part which is used to be articulated with the grinding head mount sheath, and the pitching articulation part is rigid.

The present invention also discloses a lateral grinding drill with continuously variable angle, including a tube body component and a grinding head arranged at the front end of the tube body component, the grinding head being configured to be driven to pitch and rotate on its own axis, the tube body component including an outer tube body and an inner tube body which is coaxially arranged inside the outer tube body and configured to be rotatablely fit with the outer tube body and the grinding head, the front end of the outer tube body is provided with a grinding head mount sheath configured to mount the grinding head and drive the grinding head to pitch, the back end of the grinding head mount sheath and the front end of the outer tube body forms an articulated structure of a single degree of freedom in a form that an articulation joint and an articulation groove are interconnected with each other, and a portion of the outer tube body to be articulated with the grinding head mount sheath is thickened.

Further, the front end of the outer tube body is fixedly connected with a outer tube articulation part adapted to be articulated with the grinding head mount sheath, two curved articulation joints are radially oppositely formed on the front end face of the outer tube articulation part, and two curved articulation grooves are radially oppositely formed on the tail end face of the grinding head mount sheath and configured for inserting the two curved articulation joints to form an articulated structure of a single degree of freedom; and the outer tube articulation part is located between the two curved articulation joints to form a channel through which the inner tube body passes.

The present invention also discloses a driving component for driving a lateral grinding drill with continuously variable angle to change grinding orientation, including a connection handle and a pitching driving component for driving the grinding head of the lateral grinding drill with continuously variable angle to pitch, wherein the pitching driving component includes a reciprocating middle part and a reciprocating driving part, the front end of the reciprocating middle part is connected to the grinding head in a form that the grinding head is drivable to pitch, the back end of the reciprocating middle part is drivablely fit with the reciprocating driving part at least in the axial direction, and the reciprocating driving part is fit with the connection handle in a form that the reciprocating driving part is movable relative to the connection handle connection handle.

Further, the driving component further includes a direction driving component, the direction driving component includes a connection sleeve coaxially fixed to the outer tube body of the lateral grinding drill with continuously variable angle, and a driving sleeve arranged outside the connection sleeve, the driving sleeve is fixed to the connection sleeve in the circumferential direction and is slidable to the connection sleeve in the axial direction, and the driving sleeve is configured to slide along the axial direction to engage with or disengage from the connection handle to achieve limiting or releasing in the circumferential direction.

Further, the driving sleeve is provided with a backward pretightening force which makes the driving sleeve be close to the front end of the connection handle and engage with the connection handle in the circumferential direction; the tail end of the middle tube is axially fixedly connected with a transition sleeve, a radial driving arm is arranged on the outer circle of the transition sleeve, and the radial driving arm is configured to be rotatablely fit with the reciprocating driving part in a single degree of freedom mode; the reciprocating driving part is a reciprocating driving sleeve with internal threads which match with external threads provided on the connection handle; and a necking portion is arranged on the back end of the driving sleeve, the front end of the reciprocating driving sleeve is arranged outside the outer circle of the necking portion of driving sleeve, and the back end of the reciprocating driving sleeve is arranged outside the connection handle.

The present invention has the following beneficial effects. The lateral grinding drill with continuously variable angle according to the present invention adopts a direct articulated structure to transmit the transmission between the inner tube body and the grinding head, and can implement pitching motion. A flexible transmission structure is used to compensate the axis deviation caused by the pitching and driving. The transmission structure is simple, and the transmission cycle is short, which facilitates stable control to improve the efficiency of the surgery. In addition, with the structure which can adjust the grinding head in both the pitching and circumferential positions, it achieves the universal direction adjustment of the grinding head, so that the grinding head can be adjusted in the longitudinal and circumferential positions according to the change of the surgery site, which can have a good adaptability for the surgery position and good accuracy to improve the efficiency in surgery operation, and shorten postoperative recovery time, to alleviate the suffering of the patients while reducing treatment cost.

BRIEF DESCRIPTION OF THE DRAWINGS

The present invention will be described below by reference to the following embodiments taken in conjunction with the accompanying drawings.

DETAILED DESCRIPTION OF THE PREFERRED EMBODIMENTS

Figure 1:
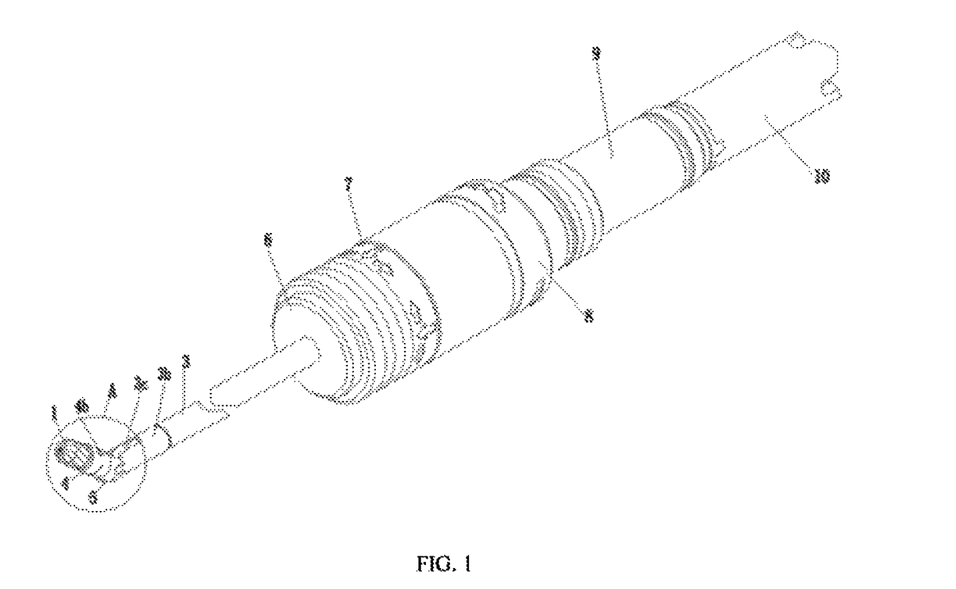
FIG. 1 is a schematic diagram showing a lateral grinding drill with continuously variable angle according to one embodiment of the present invention.
Figure 2:
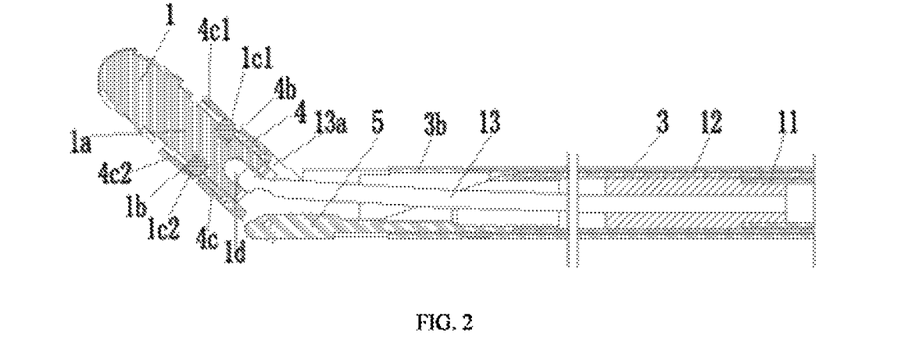
FIG. 2 is a schematic diagram showing the section of the front end of the lateral grinding drill with continuously variable angle according to one embodiment of the present invention.
Figure 3:
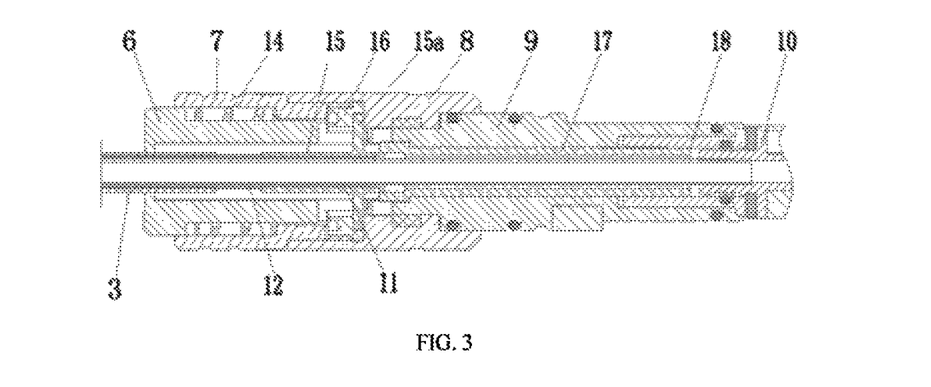
FIG. 3 is a schematic diagram showing the section of the back end of the lateral grinding drill with continuously variable angle according to one embodiment of the present invention.
Figure 4:
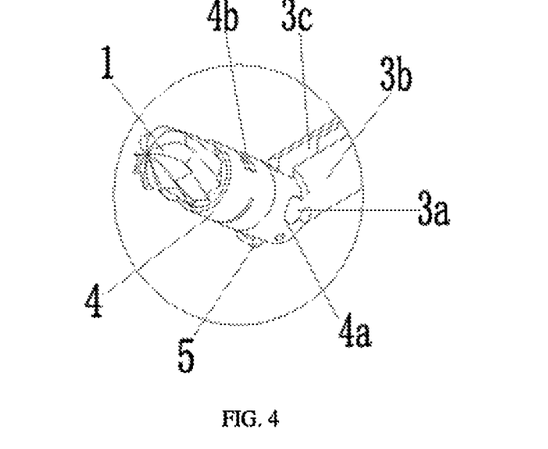
FIG. 4 is a detailed diagram of the portion contained in circle A of FIG. 1.
Figure 5:
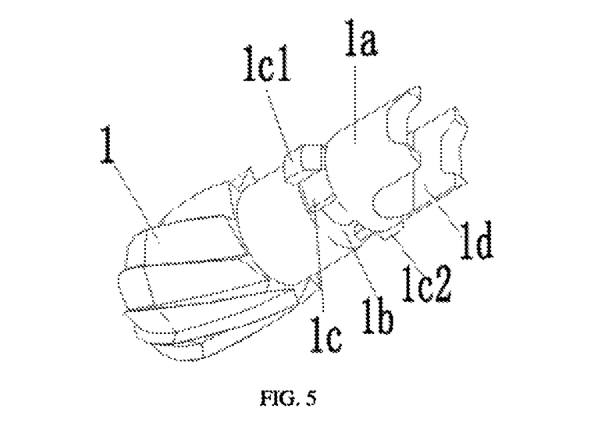
FIG. 5 is a schematic diagram showing a grinding head according to one embodiment of the present invention.
Figure 6:
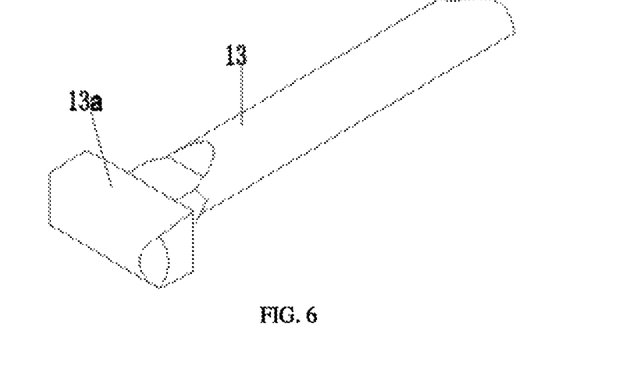
FIG. 6 is a schematic diagram showing a flexible transmission part according to one embodiment of the present invention.

FIG. 1 is a schematic diagram showing a lateral grinding drill with continuously variable angle according to one embodiment of the present invention; FIG. 2 is a schematic diagram showing the section of the front end of the lateral grinding drill with continuously variable angle according to one embodiment of the present invention; FIG. 3 is a schematic diagram showing the section of the back end of the lateral grinding drill with continuously variable angle according to one embodiment of the present invention; FIG. 4 is a detailed diagram of the portion contained in circle A of FIG. 1; FIG. 5 is a schematic diagram showing a grinding head according to one embodiment of the present invention; and FIG. 6 is a schematic diagram showing a flexible transmission part according to one embodiment of the present invention. As shown in the figures, the lateral grinding drill with continuously variable angle according to the present invention, i.e., medical grinding tool, includes a tube body component and a grinding head 1 arranged at the front end of the tube body component, the grinding head 1 being configured to be driven to pitch and rotate on its own axis, wherein the tube body component includes an outer tube body 3 and an inner tube body 11 which is coaxially arranged inside the outer tube body 3 and configured to be rotatablely fit with the outer tube body 3 and the grinding head 11, the tail end of the grinding head 1 is articulated to the inner tube body 11 along the circumferential direction in a form of transmission, and a flexible transmission part 13 is arranged at least on the front end of the inner tube body 11 , which is configured to be articulated to the tail end of the grinding head 1 and be able to transmit torque. The pitching described here means rotating at a certain angle to the axis of the tube body component. The grinding head rotating on its own axis described here means the grinding head is driven to rotate for grinding. The grinding head can be adjusted to be coaxial with the tube body component when it is used, and can be adjusted to a position of suitable pitch angle for grinding according to the need after it enters into a working circumstance. The grinding head may carry out grinding after pitching. The transmission means adapting the change of the transmission axis through the flexible transmission part.

In the embodiment, an articulation groove 1d with an opening end is formed at the tail end of the grinding head 1, and the front end of the flexible transmission part 13 is provided with a rod-shaped articulation portion 13a which is configured to be rotatably fit with the flexible transmission part and articulated and fit with the articulation groove. In addition to having the flexible transmission part 13 to fit the rotation of the grinding head on its own axis driven after the pitching operation, there is some movement space between the articulation groove 1d and the rod-shaped articulation portion 13a to fit the length difference generated after the pitching operation, so the rotation may be smooth, and the inner tube body 11 and the flexible transmission part 13 can be drew form the outer tube body 2 to be convenient for assembly and disassemble.

In the embodiment, the rod-shaped articulation portion 13a and the flexible transmission part 13 form a T-shaped structure. In this way, it may not only ensure the transmission strength of the articulated structure, but also make the outer tube body 3 pass smoothly after its articulated position for pitching has been thickened inwards. Of course, the articulation portion of such structure can also be available for an articulation groove without an opening.

In the embodiment, the root of the connection between the flexible transmission part and the rod-shaped articulation portion is necking on the T-shaped plane. Such structure can be adapted to the structure of the articulation groove and not interfere with the groove wall of the articulation groove 1d, when the rod-shaped articulation portion 13a moves laterally and rotationally from the articulation groove 1d after the rod-shaped articulation portion 13a being articulated to the articulation groove 1d.

In the embodiment, the grinding head 1 is provided with a grinding head handle 1a, and the articulation groove 1d is located on the tail end of the grinding head handle 1a. The front end of the outer tube body 3 is articulated with a grinding head mount sheath 4 in a single degree of freedom mode, the grinding head handle 1a is arranged inside the grinding head mount sheath 4 and configure to be rotatably fit with the grinding head mount sheath 4 in a single degree of freedom mode, and the grinding head 1 has a grinding blade extending out of the grinding head mount sheath 4. The fit mode of rotatably fitting in a single degree of freedom can be any mechanical means which can achieve this structure, including axial mechanical position-limiting. With the structure of the grinding head handle 1a, it is convenient for installation and assembly, can assure the structure compactness, and is appropriate for this filed, and the grinding head can be driven by the grinding head mount sheath 4 to implement pitching action. The flexible transmission part 13 is connected to the front end of the inner tube body 11 through threaded connection or locking connection, with a good adaptation, and the flexible transmission part can be replaced according to needs to ensure the long-term operation of the tool. The rod-shaped articulation portion 13a is integrally formed on the front end of the flexible transmission part 13. The articulation in a single degree of freedom mode means that the relative motion between the parts articulated together is limited in the transmission direction of the articulation, and the means for articulation can be an existing articulated structure with shaft. Since such structure tends to be small, it is appropriate to provide an articulation groove on a part, and process a rod-shaped structure matching with the articulation groove or two radially symmetric ball structures on another part. As shown in FIG. 4, two curved articulation joints 3a are radially oppositely formed on the front end face of the outer tube body 3, and two curved articulation grooves 4a are radially oppositely formed on the tail end face of the grinding head mount sheath 4 and configured for inserting the two curved articulation joints 3a to form an articulated structure of a single degree of freedom. In this way, it is simple in structure, convenient for processing, flexible for the articulation to rotate, and easy to disassemble. In addition, this structure makes the axis of the outer tube body and the axis of the articulation be located on the same plane.

As shown in the figures, the grinding head handle 1a has axial movement space after being articulated to the flexible transmission part 13, to form a complete open articulated structure which is formed by inserting the rod-shaped articulation portion 13a into the articulation groove 1d directly and has axial movement space to make the relative movement between the grinding head handle 1a and the rod-shaped articulation portion 13a smooth, so that the inner tube body 11 and the flexible transmission part 13 can be drawn out at any time to facilitate cleaning and maintenance. This structure removes the universal shaft structure of the existing technologies, achieves the compactness of the structure and reduction of the volume, and is more applicable for deep and narrow space.

In the embodiment, the outer tube body is configured to be driven to rotate along the circumferential direction, so that the grinding head mount sheath and grinding head are configured to be driven to revolute. The revolution described here means the whole grinding head 1 rotates around the axis of the tube body component in order to achieve universal grinding, that is, pitching motion and circumferential motion can be achieved, as two degrees of freedom, and can be combined to form a plurality of working conditions in different directions. The grinding head can be adjusted to be coaxial with the tube body component when it is used, and can be adjusted to a position of suitable pitch angle for grinding according to the need after it enters into a working circumstance.

In the embodiment, the lateral grinding drill with continuously variable angle further includes a connection handle 9 and a driving component, and the driving component includes a pitching driving component for driving the grinding head mount sheath 4 to pitch and a direction driving component for driving the outer tube body to rotate along the circumferential direction.

The pitching driving component includes a reciprocating middle part and a reciprocating driving part 8, the front end of the reciprocating middle part is connected to the grinding head mount sheath 4 in a form that the grinding head mount sheath 4 is drivable to pitch, in order to drive the grinding head mount sheath 4 to rotate in the pitching articulation direction, to drive the grinding head 1 to implement pitching motion. The back end of the reciprocating middle part is drivablely fit with the reciprocating driving part 8 at least in the axial direction, and the reciprocating driving part 8 is fit with the connection handle 9 in a form that the reciprocating driving part 8 is movable relative to the connection handle connection handle 9, in order to drive the reciprocating middle part to implement reciprocating motion to achieve the pitching motion of the grinding head mount sheath 4. The reciprocating driving part 8 may be fit with the connection handle 9 in a form that the reciprocating driving part 8 is movable relative to the connection handle connection handle 9, or through thread fitting or in a form of other reciprocating motions and being positioned at any time.

The direction driving component includes a connection sleeve 6 coaxially fixed to the outer tube body of the grinding tool, and a driving sleeve 7 arranged outside the connection sleeve, the driving sleeve is fixed to the connection sleeve in the circumferential direction and is slidable to the connection sleeve in the axial direction. The outer tube body 3 is connected to the connection sleeve 6 by welding. The relative sliding of the connection sleeve 6 to the driving sleeve 7 can be achieved by an axial flat key or the cooperation of splines, it is not explained here. The driving sleeve 7 is configured to slide along the axial direction to engage with or disengage from the connection handle 9 to achieve limiting or releasing in the circumferential direction. In this structure, the front end of the connection handle 9 can be provided with end face splines, and the tail end of the driving sleeve 7 is also provided with end face splines. When the driving sleeve 7 is driven by external force to axially slide, the driving sleeve 7 can be manually driven to drive the connection sleeve 6 to rotate, so as to drive the outer tube body 3 to rotate, and make the grinding head to implement revolution. The function of universal direction can be achieved by combining the revolution with the rotation of the grinding head 1 on its axis and the pitching motion.

In the embodiment, the driving sleeve 7 is provided with a backward pretightening force which makes the driving sleeve 7 be close to the front end of the connection handle 9 and engage with the connection handle 9 in the circumferential direction. The pretightening force may be achieved by a spring or snap spring. The engagement is achieved by the pretightening force to avoid the mistake operation and the detachment problem at runtime. As shown in the figures, a spring cavity is arranged on the inner circle of the driving sleeve 7, a columnar spring is arranged outside of the connection sleeve 6, two ends of the columnar spring press against an outer boss formed on the outer circle of the connection sleeve 6, and an inner boss formed on the inner circle of the driving sleeve 7 respectively. The tail end of the reciprocating middle part is axially fixedly connected with a transition sleeve 15, a radial driving arm 15*a* is arranged on the outer circle of the transition sleeve 15, and the radial driving arm 15*a* is configured to be rotatably fit with the reciprocating driving part 8 in a single degree of freedom mode. As shown in the figures, the radial driving arm 15*a* is axially fixed through a pressing sleeve 16 matching with the reciprocating driving part 8 in screw thread. The reciprocating driving part 8 is a reciprocating driving sleeve with internal threads which match with external threads provided on the connection handle 9. A necking portion is arranged on the back end of the driving sleeve, the front end of the reciprocating driving sleeve is arranged outside the outer circle of the necking portion of driving sleeve, and the back end of the reciprocating driving sleeve is arranged outside the connection handle. Through rotating the reciprocating driving sleeve and driving the radial driving arm 15*a* to implement reciprocating motion, it can achieve smooth and accurate operations to avoid pause and transition in the existing technologies. Meanwhile, the screw thread fitting makes the components have compactedness and integrity. The back end of the driving sleeve 7 is provided with the necking portion, the front end of the reciprocating driving sleeve is arranged outside the outer circle of the necking portion of driving sleeve 7, a step is formed on the inner circle of the front end of the reciprocating driving sleeve, the step is connected to a press cover to form a circular groove. As shown in the figures, the radial driving arm 15*a* is inserted into the circular groove to form a fitting structure which is fixed in the axial direction and slidable in the circumferential direction. Of course, there may be a plurality of radial driving arms 15*a* arranged along the circumferential direction. As shown in the figures, two radial driving arms arranged symmetrically can transmit driving force uniformly. The radial driving arm is located between the driving sleeve and the connection connection handle 9, and between the driving sleeve and the reciprocating driving sleeve, so the radial driving arm should be kept away from the end face splines between the driving sleeve 7 and the connection handle 9, to avoid motion interference. The back end of the reciprocating driving sleeve is arranged outside the connection handle 9, as shown in the figures, the back end of the reciprocating driving sleeve is arranged outside the connection handle and is fit with the connection handle by threads, facilitating the operation.

The tail end of the lateral grinding drill with continuously variable angle is provided with a connector 10 connected with the power supply, and the inner surface of the connection handle 9 is provided with a support as the supporting transition sleeve 17 shown in FIG. 3, for supporting the connector 10. The front end of the supporting transition sleeve 17 is arranged outside and rotatably fit with the transition sleeve 15, and the back end of the supporting transition sleeve 17 is arranged inside and rotatably fit with the seal transition sleeve 18. The seal transition sleeve 18 is in a rotatable fit, and provided with a necessary seal ring and slide bearing, and it is not explained here.

The present invention also discloses a special embodiment of a lateral grinding drill with continuously variable angle, including a tube body component and a grinding head 1 arranged at the front end of the tube body component, the grinding head being configured to be driven to pitch and rotate on its own axis, the tube body component including an outer tube body 3 and an inner tube body 11 which is coaxially arranged inside the outer tube body 3 and configured to be rotatably fit with the outer tube body 3 and the grinding head 1, the front end of the outer tube body being articulated with a grinding head mount sheath 4 in a single degree of freedom mode, the grinding head 1 being provided with a grinding head handle 1*a*, the grinding head handle 1*a* is provided with a position-limiting ring 1*c* which is configured to be rotatably fit with the grinding head handle 1*a* in a single degree of freedom mode, and the grinding head handle 1*a* is arranged inside the grinding head mount sheath 4 through the position-limiting ring 1*c* in an axial position-limiting form. In this way, the structure is simple, and is easy for disassembly and assembly. The grinding head handle 1*a* can be inserted into the grinding head mount sheath 4 directly to achieve axial position-limiting. The mode of inserting into a circular groove can be mostly used in the form of rotatable fit in a single degree of freedom.

In the embodiment, the grinding head mount sheath 4 includes an outer sleeve and an inner sleeve 4*c* arranged inside the outer sleeve, the position-limiting ring 1*c* is provided with two radially symmetric position-limiting bulges 1*c*1, 1*c*2, the outer circle of the grinding head handle 1*a* is provided with an annular position-limiting groove 1*b* configured to make the position-limiting ring 1*c* into place and have radical movement space, and the rotatable fit in a single degree of freedom is achieved by inserting the position-limiting ring 1*c* into the annular position-limiting groove 1*b*. The inner sleeve 4*c* is provided with two radially symmetric axial opening grooves 4*c*1, 4*c*2, the outer sleeve is provided with a position-limiting through hole 4*b* radially passing through the outer sleeve, and the outer sleeve is an opening sleeve with an axial opening. The grinding head handle 1a is arranged inside the inner sleeve 4c, two position-limiting bulges 1c1, 1c2 of the position-limiting ring 1c are fit along the axial opening grooves, one position-limiting bulge 1c1 is inserted into the position-limiting through hole, and the other position-limiting bulge 1c2 abuts on the inner wall of the outer sleeve. The outer sleeve of the grinding head mount sheath 4 has an axial opening, so it has radial elasticity to secure the position-limiting ring 1c. As shown in FIG. 2, the axial opening of the outer sleeve is arranged on the outer sleeve at an angle of 45° to the position-limiting through hole. When installing, the grinding head handle 1a and the position-limiting ring 1c are arranged inside the inner sleeve 4c together, two position-limiting bulges 1c1, 1c2 are radially limited and compressed, and when the position-limiting ring 1c slides into the installation position, one position-limiting bulge 1c1 is inserted into the position-limiting through hole of the position-limiting bulge 1c1, to achieve axial position-limiting. When removing, the position-limiting bulge 1c1 in the position-limiting through hole is radially pressed, the position-limiting ring 1c (the position-limiting ring is an opening ring which is convenient to install into the annular position-limiting groove 1b and convenient to deform) itself and the outer sleeve can be deformed, the position-limiting bulge 1c1 can be radially inwardly disengaged from the inside diameter of the position-limiting through hole 4b, and the grinding head handle can be removed. As shown in the figures, the outer sleeve is not only provided with an axial opening, but also provided with a circumferential groove in the circumferential direction. The circumferential groove has an opening at the edge of the axial opening groove to reduce difficulty of assembly and disassembly.

The lateral grinding drill with continuously variable angle according to this embodiment can be combined with the above technical solution for use, to obtain the better effect.

The present invention also discloses a lateral grinding drill with continuously variable angle, including a tube body component and a grinding head arranged at the front end of the tube body component, the grinding head 1 being configured to be driven to pitch and rotate on its own axis, the tube body component including an outer tube body 3 and an inner tube body 11 which is coaxially arranged inside the outer tube body 3 and configured to be rotatablely fit with the outer tube body 3 and the grinding head 1, the front end of the outer tube body 3 being articulated with a grinding head mount sheath 4 in a single degree of freedom mode, the grinding head 1 being mounted on the grinding head mount sheath 4 and configure to be rotatablely fit with the grinding head mount sheath 4 along the circumferential direction, and the grinding head 1 having a grinding blade extending out of the grinding head mount sheath 4; and the grinding head mount sheath 4 is provided with a reciprocating middle part configured to drive the grinding head mount sheath to pitch in the rotation direction of the articulation, and the reciprocating middle part at least has movement space in the direction of the pitching motion of the grinding head mount sheath, to accommodate the radial movement of the reciprocating driving part caused by the pitching motion of the grinding head mount sheath 4 after being articulated directly, to avoid interference. In this way, the structure is simple and useful.

In the embodiment, the reciprocating middle part is a middle tube body 12 located between the inner tube body 11 and the outer tube body 3, there is radical movement space between the middle tube body 12 and the inner tube body 11, and between the middle tube body 12 and the outer tube body 3, the radical movement space accommodates the radial displacement caused by the middle tube body when the grinding head mount sheath 4 is pitching; and the front end of the middle tube body 12 extends forward to form a pitching articulation part 5 which is used to be articulated with the grinding head mount sheath, and the pitching articulation part 5 is rigid. In this way, the middle tube body 12 can use the radical movement space to accommodate the small radical displacement when the grinding head mount sheath is pitching, and the rigid structure of the pitching articulation part can smoothly drive the grinding head mount sheath to pitch. The structure is simple and compact to avoid the increase in volume caused by a complex structure, to ensure the success of the surgery. As shown in the figures, the pitching articulation part 5 is rigid, and is a thickened structure.

The pitching articulation part 5 is formed on a pup joint which is fixedly connected to the middle tube body, and the pitching articulation part 5 can be also formed in the middle tube body directly, which does not affect the purpose of the present invention. Since this embodiment can be combined with the above technical solutions, the rail end of the middle tube body 12 is axially fixedly connected to the above transition sleeve 15, the outer circle of the transition sleeve 15 is provided with a radial driving arm 15a. In the embodiment, the transition sleeve 15 is connected with the middle tube body 12 by welding, and the transition sleeve 15 and the radial driving arm 15a are formed integrally. The radial driving arm 15a is rotatably fit with the reciprocating driving part in a single degree of freedom mode to achieve forward and backward driving. In this way, the structure is simple and compact, and is convenient for assembly and disassembly.

The present invention also discloses a special embodiment of a lateral grinding drill with continuously variable angle, including a tube body component and a grinding head 1 arranged at the front end of the tube body component, the grinding head being configured to be driven to pitch and rotate on its own axis, the tube body component including an outer tube body 3 and an inner tube body 11 which is coaxially arranged inside the outer tube body 3 and configured to be rotatablely fit with the outer tube body 3 and the grinding head 1, the front end of the outer tube body 3 is provided with a grinding head mount sheath 4 configured to mount the grinding head 1 and drive the grinding head 1 to pitch, the back end of the grinding head mount sheath 4 and the front end of the outer tube body forms an articulated structure of a single degree of freedom in a form that an articulation joint and an articulation groove are interconnected with each other, and a portion of the outer tube body 3 to be articulated with the grinding head mount sheath 4 is thickened. Such design make the articulated structure have enough thickness to increase the strength, and there is a narrow passage in the middle of the articulated structure. The thickened structure facilitates the bending portion to bear greater lateral bending moment during grinding, to ensure the success of the surgery.

In the embodiment, the portion of the outer tube body 3 to be articulated with the grinding head mount sheath 4 is provided with an outer tube articulation part 3b for the fixed connection of the front end of the outer tube body 3, and the outer tube body 3 can be connected to the outer tube articulation part 3b through screw threads or by welding, which is not explained here. Two curved articulation joints 3a are radially oppositely formed on the front end face 3c of the outer tube articulation part 3b, and two curved articulation grooves 4a are radially oppositely formed on the tail end face of the grinding head mount sheath 4 and configured for inserting the two curved articulation joints 3a to form an articulated structure of a single degree of freedom. The outer tube articulation part 3b is located between the two curved articulation joints 3a to form a channel through which the inner tube body 11 passes. The outer tube articulation part 3b is thickened in the channel radially inwards. The special shape of the head of the inner tube body 11 (including the flexible transmission part 13) is designed so that it can pass through the narrow channel (caused by thickening) between the curved articulation joints, be kept away from the two curved articulation joints and the front grinding head to form a universal joint to rotation drive. In this structure, the articulation joint is thickened, and the connection structure of the outer tube articulation part 3b and the outer tube body 3 is used, so it not only increases the strength, but also facilitates assembly.

The present invention also discloses a driving component for driving a lateral grinding drill with continuously variable angle to change grinding orientation, including a connection handle 9 and a pitching driving component for driving the grinding head 1 of the lateral grinding drill with continuously variable angle to pitch, wherein the pitching driving component includes a reciprocating middle part and a reciprocating driving part 8, the front end of the reciprocating middle part is connected to the grinding head 1 in a form that the grinding head 1 is drivable to pitch, the back end of the reciprocating middle part is drivablely fit with the reciprocating driving part 8 at least in the axial direction, and the reciprocating driving part 8 is fit with the connection handle 9 in a form that the reciprocating driving part is movable relative to the connection handle connection handle.

Further, the driving component further includes a direction driving component, the direction driving component includes a connection sleeve 6 coaxially fixed to the outer tube body 3 of the lateral grinding drill with continuously variable angle, and a driving sleeve 7 arranged outside the connection sleeve 6, the driving sleeve 7 is fixed to the connection sleeve 6 in the circumferential direction and is slidable to the connection sleeve 6 in the axial direction, and the driving sleeve 7 is configured to slide along the axial direction to engage with or disengage from the connection handle 9 to achieve limiting or releasing in the circumferential direction.

Further, the driving sleeve 7 is provided with a backward pretightening force which makes the driving sleeve 7 be close to the front end of the connection handle 9 and engage with the connection handle 9 in the circumferential direction; the tail end of the middle tube is axially fixedly connected with a transition sleeve 15, a radial driving arm 15a is arranged on the outer circle of the transition sleeve 15, and the radial driving arm 15a is configured to be rotatably fit with the reciprocating driving part 8 in a single degree of freedom mode; the reciprocating driving part 8 is a reciprocating driving sleeve with internal threads which match with external threads provided on the connection handle 9; and a necking portion is arranged on the back end of the driving sleeve 7, the front end of the reciprocating driving sleeve is arranged outside the outer circle of the necking portion of driving sleeve 7, and the back end of the reciprocating driving sleeve is arranged outside the connection handle 9.

Each of the above preferred embodiments of the present invention can form a single technical solution, and it should be understood for those skilled in the art that all the above preferred embodiments can be combined to achieve the purpose of the present invention, that is, the aforementioned structures can be independently formed a technical solution or be combined to be applied in the lateral grinding drill of the present invention, which is not explained here.

The above are preferred embodiments of the present invention described in detail, and should not be deemed as limitations to the scope of the present invention. It should be noted that variations and improvements will become apparent to those skilled in the art to which the present invention pertains without departing from its spirit and scope. Therefore, the scope of the present invention is defined by the appended claims.

What is claimed is:

1. A lateral grinding drill with continuously variable angle, comprising a tube body component and a grinding head arranged at the front end of the tube body component, the grinding head being configured to be driven to pitch and rotate on its own axis, wherein the tube body component comprises an outer tube body and an inner tube body which is coaxially arranged inside the outer tube body and configured to be rotatablely fit with the outer tube body and the grinding head, the tail end of the grinding head is articulated to the inner tube body along the circumferential direction in a form of transmission, and a flexible transmission part is arranged at least on the front end of the inner tube body, which is configured to be articulated to the tail end of the grinding head and be able to transmit torque.

2. The lateral grinding drill with continuously variable angle of claim 1, wherein an articulation groove with an opening end is formed at the tail end of the grinding head, and the front end of the flexible transmission part is provided with a rod-shaped articulation portion which is configured to be rotatablely fit with the flexible transmission part and articulated and fit with the articulation groove.

3. The lateral grinding drill with continuously variable angle of claim 2, wherein the grinding head is provided with a grinding head handle, and the articulation groove is located on the tail end of the grinding head handle; the front end of the outer tube body is articulated with a grinding head mount sheath in a single degree of freedom mode, the grinding head handle is arranged inside the grinding head mount sheath and configure to be rotatablely fit with the grinding head mount sheath in a single degree of freedom mode, and the grinding head has a grinding blade extending out of the grinding head mount sheath; and the flexible transmission part is connected to the front end of the inner tube body, and the rod-shaped articulation portion is integrally formed on the front end of the flexible transmission part.

4. The lateral grinding drill with continuously variable angle of claim 3, wherein the outer tube body is configured to be driven to rotate along the circumferential direction, so that the grinding head mount sheath and grinding head are configured to be driven to revolute.

5. The lateral grinding drill with continuously variable angle of claim 4, further comprises a connection handle and a driving component, wherein driving component comprises a pitching driving component for driving the grinding head mount sheath to pitch and a direction driving component for driving the outer tube body to rotate along the circumferential direction;

the pitching driving component comprises a reciprocating middle part and a reciprocating driving part, the front end of the reciprocating middle part is connected to the grinding head mount sheath in a form that the grinding head mount sheath is drivable to pitch, the back end of the reciprocating middle part is drivablely fit with the reciprocating driving part at least in the axial direction, and the reciprocating driving part is fit with the connection handle in a form that the reciprocating driving part is movable relative to the connection handle connection handle; and the direction driving component comprises a connection sleeve coaxially fixed to the outer tube body, and a driving sleeve arranged outside the connection sleeve, the driving sleeve is fixed to the connection sleeve in the circumferential direction and is slidable to the connection sleeve in the axial direction, and the driving sleeve is configured to slide along the axial direction to engage with or disengage from the connection handle to achieve limiting or releasing in the circumferential direction.

6. The lateral grinding drill with continuously variable angle of claim 5, wherein the driving sleeve is provided with a backward pretightening force which makes the driving sleeve be close to the front end of the connection handle and engage with the connection handle in the circumferential direction; the tail end of the reciprocating middle part is axially fixedly connected with a transition sleeve, a radial driving arm is arranged on the outer circle of the transition sleeve, and the radial driving arm is configured to be rotatablely fit with the reciprocating driving part in a single degree of freedom mode; the reciprocating driving part is a reciprocating driving sleeve with internal threads which match with external threads provided on the connection handle; and a necking portion is arranged on the back end of the driving sleeve, the front end of the reciprocating driving sleeve is arranged outside the outer circle of the necking portion of driving sleeve, and the back end of the reciprocating driving sleeve is arranged outside the connection handle.

7. The lateral grinding drill with continuously variable angle of claim 1, wherein an articulation groove is formed at the tail end of the grinding head, the front end of the flexible transmission part is provided with a rod-shaped articulation portion which is configured to be rotatablely fit with the flexible transmission part and articulated and fit with the articulation groove, the rod-shaped articulation portion and the flexible transmission part form a T-shaped structure.

8. The lateral grinding drill with continuously variable angle of claim 7, wherein the root of the connection between the flexible transmission part and the rod-shaped articulation portion is necking on the T-shaped plane.

9. A lateral grinding drill with continuously variable angle, comprising a tube body component and a grinding head arranged at the front end of the tube body component, the grinding head being configured to be driven to pitch and rotate on its own axis, the tube body component including an outer tube body and an inner tube body which is coaxially arranged inside the outer tube body and configured to be rotatablely fit with the outer tube body and the grinding head, the front end of the outer tube body being articulated with a grinding head mount sheath in a single degree of freedom mode, the grinding head being provided with a grinding head handle, the grinding head handle is provided with a position-limiting ring which is configured to be rotatablely fit with the grinding head handle in a single degree of freedom mode, and the grinding head handle is arranged inside the grinding head mount sheath through the position-limiting ring in an axial position-limiting form.

10. The lateral grinding drill with continuously variable angle of claim 9, wherein the grinding head mount sheath comprises an outer sleeve and an inner sleeve arranged inside the outer sleeve, the position-limiting ring is provided with two radially symmetric position-limiting bulges, the outer circle of the grinding head handle is provided with an annular position-limiting groove configured to make the position-limiting ring into place and have radical movement space, the inner sleeve is provided with two radially symmetric axial opening grooves, the outer sleeve is provided with a position-limiting through hole radially passing through the outer sleeve, and the outer sleeve is an opening sleeve with an axial opening; and the grinding head handle is arranged inside the inner sleeve, two position-limiting bulges of the position-limiting ring are fit along the axial opening grooves, one of the position-limiting bulges is inserted into the position-limiting through hole, and the other position-limiting bulge abuts on the inner wall of the outer sleeve.

11. A lateral grinding drill with continuously variable angle, comprising a tube body component and a grinding head arranged at the front end of the tube body component, the grinding head being configured to be driven to pitch and rotate on its own axis, the tube body component including an outer tube body and an inner tube body which is coaxially arranged inside the outer tube body and configured to be rotatablely fit with the outer tube body and the grinding head, the front end of the outer tube body being articulated with a grinding head mount sheath in a single degree of freedom mode, the grinding head being mounted on the grinding head mount sheath and configure to be rotatablely fit with the grinding head mount sheat along the circumferential direction, and the grinding head having a grinding blade extending out of the grinding head mount sheath; and the grinding head mount sheath is provided with a reciprocating middle part configured to drive the grinding head mount sheath to pitch in the rotation direction of the articulation, and the reciprocating middle part at least has movement space in the direction of the pitching motion of the grinding head mount sheath.

12. The lateral grinding drill with continuously variable angle of claim 11, wherein the reciprocating middle part is a middle tube body located between the inner tube body and the outer tube body, there is radical movement space between the middle tube body and the inner tube body, and between the middle tube body and the outer tube body, the radical movement space accommodates the radial displacement caused by the middle tube body when the grinding head mount sheath is driven to pitch; and the front end of the middle tube body extends forward to form a pitching articulation part which is used to be articulated with the grinding head mount sheath, and the pitching articulation part is rigid.

13. previously presented) A lateral grinding drill with continuously variable angle, comprising a tube body component and a grinding head arranged at the front end of the tube body component, the grinding head being configured to be driven to pitch and rotate on its own axis, the tube body component including an outer tube body and an inner tube body which is coaxially arranged inside the outer tube body and configured to be rotatablely fit with the outer tube body and the grinding head, the front end of the outer tube body is provided with a grinding head mount sheath configured to mount the grinding head and drive the grinding head to pitch, the back end of the grinding head mount sheath and the front end of the outer tube body forms an articulated structure of a single degree of freedom in a form that an articulation joint and an articulation groove are interconnected with each other, and a portion of the outer tube body to be articulated with the grinding head mount sheath is thickened.

14. The lateral grinding drill with continuously variable angle of claim 13, wherein the portion of the outer tube body to be articulated with the grinding head mount sheath is provided with an outer tube articulation part for the fixed connection of the front end of the outer tube body, two curved articulation joints are radially oppositely formed on the front end face of the outer tube articulation part, and two curved articulation grooves are radially oppositely formed on the tail end face of the grinding head mount sheath and configured for inserting the two curved articulation joints to form an articulated structure of a single degree of freedom; and the outer tube articulation part is located between the two curved articulation joints to form a channel through which the inner tube body passes, and the thickening of the outer tube articulation part is radially inward in the channel.

* * * * *